(12) United States Patent
Lichtblau et al.

(10) Patent No.: US 6,590,109 B2
(45) Date of Patent: Jul. 8, 2003

(54) METHOD FOR ISOLATING TERPENE TRILACTONES (GINKGOLIDES, BILOBALIDE) FROM LEAVES AND PHARMACEUTICAL POWDERS OF GINKGO BILOBA

(75) Inventors: Dirk Lichtblau, Halle/S. (DE); Nina Berova, New York, NY (US); John Berger, Oro Valley, AZ (US); Koji Nakanishi, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 10/194,089

(22) Filed: Jul. 11, 2002

(65) Prior Publication Data

US 2003/0031736 A1 Feb. 13, 2003

Related U.S. Application Data

(63) Continuation-in-part of application No. 09/903,049, filed on Jul. 11, 2001, now abandoned.

(51) Int. Cl.⁷ ...................... C07D 307/93; C07D 407/14
(52) U.S. Cl. ........................ 549/297; 549/298
(58) Field of Search ................... 549/297, 298

(56) References Cited

U.S. PATENT DOCUMENTS

| 4,981,688 | A | 1/1991 | Ayroles et al. |
| 5,389,370 | A | 2/1995 | O'Reilley et al. |
| 5,399,348 | A | 3/1995 | Schwabe |
| 5,512,286 | A | 4/1996 | Schwabe |
| 6,030,621 | A | 2/2000 | De Long et al. |
| 6,117,431 | A | 9/2000 | Ramazanov et al. |
| 6,143,725 | A | 11/2000 | Vasella et al. |
| 6,174,531 | B1 | 1/2001 | Zhang et al. |
| 6,187,314 | B1 | 2/2001 | Xie et al. |
| 6,221,356 | B1 | 4/2001 | Junsheng |
| 6,274,621 | B1 | 8/2001 | Drieu |
| 6,328,999 | B1 | 12/2001 | Schwabe |

FOREIGN PATENT DOCUMENTS

WO   02083158   10/2002

*Primary Examiner*—Taofiq Solola
(74) *Attorney, Agent, or Firm*—John P. White; Cooper & Dunham LLP (57) ABSTRACT

A method of isolating terpene trilactones from *Ginkgo biloba* plant material or extract comprising the steps of suspending the plant material or extract in either water or an aqueous solution of an oxidation reagent; extracting the terpene trilactones using an acceptable extraction agent; separating the organic layer from the aqueous layer; washing the organic layer with an acceptable aqueous salt or hydroxide solution, which may be an alkaline solution; and drying the organic layer to form a dried extract containing terpene trilactones. Further purification by treatment with or filtration over activated charcoal, by treatment with or filtration over alumina and by recrystallization with an acceptable solvent or solvent mixture leads to extracts with a content of terpene trilactones higher than 50%. Unwanted levels of ginkgolic acids are reduced to acceptable levels by reversed phase chromatography.

71 Claims, 9 Drawing Sheets

FIGURE 3  From commercial powder with 5-8% of terpene trilactones(ginkgolides A/B/C/J and bilobalide)

FIGURE 4    20 ml oxidation solution, 10 min boiling, only 1st extraction (15 ml EtOAc), washing with sat. NaHCO₃, sat. Na₂S₂O₃ and sat. NaCl (15 ml each).

Optimized extraction protocol for dried leaves.

METHOD FOR ISOLATING TERPENE TRILACTONES (GINKGOLIDES, BILOBALIDE) FROM LEAVES AND PHARMACEUTICAL POWDERS OF GINKGO BILOBA

This application is a continuation-in-part of U.S. Ser. No. 09/903,049, filed Jul. 11, 2001 now abandoned, the contents of which are hereby incorporated by reference.

Throughout this application various publications are referenced in parenthesis. The disclosures of these publications in their entireties are hereby incorporated by reference into this application in order to more fully describe the state of the art to which this invention pertains.

BACKGROUND OF THE INVENTION

*Ginkgo biloba* fruits and seeds have been long used in Chinese folk medicine. The first mentioning of such a use appeared in the book of Liu Wen-Tai in 1505 in China. In the 1960's the structures of the active components have been analyzed. Around the same time, in 1965 the first leaf preparations were placed in modern medicine by the Willmar Schwabe AG, Germany. In 1971 after a collaboration between the Willmar Schwabe AG, Germany and the Beuafour group (IPSEN) in France the first concentrated and standardized extract EGb761 (Germany 1971: DE 2117429 C3 and France 1972: 72.12288) were launched and commercialized as Tanakan (France) and Tebonin Forte (Germany). Following the European application, in 1977 a leaf extract was described in the Medical Dictionary of the Republic of China. During the next decade other companies also placed similar products on the market. Today, *Ginkgo biloba* leaf extracts are found in several kinds of products, such as food supplements and energy pills, homeopathic uses, juices, cosmetics, various tea preparation, cigarettes, Ginkgo wine or and even in potato snacks referred to as the 'memory snack'. The biological activities from the extracts are diverse and known to be effective in: increasing short-term memory, treatment of cerebral insufficiency and dementia, beneficial effects as an antiasthmatic and against polyuria or tinitus, PAF-inhibitor and improving the blood flow, vaso-protection and radical scavenging.

Since the current extract Egb761 contains only between 5–7% of this terpene trilactones, the extract is only used as a food and health supplement. In order to further enhance the market for *Ginkgo biloba* products, the interest is geared towards extracts with higher purity. In contrast to the large number of patents, where the extraction procedure is rather complicated or the terpene trilactones can only be obtained in a low purity, disclosed herein is a simple extraction procedure for producing a terpene trilactones concentration that is 10-fold higher. Disclosed is a method of isolation and concentration of the terpene trilactones from leaves of the tree *Ginkgo biloba* or from pharmaceutical powder can be used on the industrial scale.

SUMMARY OF THE INVENTION

Disclosed is a method of isolating terpene trilactones from *Ginkgo biloba* plant material or extract comprising the steps of suspending the plant material or extract in either water or an aqueous solution of an oxidation reagent; extracting the terpene trilactones using an acceptable extraction agent; separating the organic layer from the aqueous layer; washing the organic layer with an acceptable aqueous salt solution, which may be an alkaline solution; and drying the organic layer to form a dried extract containing terpene trilactones. Further processing by reversed phase chromatography of the extracts with polymeric resins reduces the level of undesirable ginkgolic acids to amounts less than 10 ppm.

BRIEF DESCRIPTION OF THE FIGURES

FIG. 7 Amounts and distribution patter of TTLs prepared from A) Bioginkgo™ powder; B) dried yellow leaves; and C) dried green leaves.

DETAILED DESCRIPTION OF THE INVENTION

One embodiment of the subject invention is a method of isolating terpene trilactones from *Ginkgo biloba* plant material or extract comprising the steps of:

suspending the plant material or extract in the presence of an oxidation reagent, extracting the terpene trilactones using an acceptable extraction agent, and separating the organic layer from the aqueous layer to thereby isolate the terpene trilactones in the organic layer. The oxidation reagent may be in aqueous solution.

In the method, the aqueous solution may contain 0.1% to 50% oxidation reagent, preferably 0.1% to 30%, more preferably 1% to 20%, yet more preferably 2% to 15%, most preferably 3% to 5%. The oxidation reagent may be any oxidizing agent, and can be 3-chloroperbenzoic acid (MCPBA), $MnO_2$, or hydrogen peroxide. The oxidation reagent is preferably hydrogen peroxide.

In the method, the aqueous solution may further comprises an acid. The amount of acid in the aqueous solution may be from about 0.1% to 15%, or as otherwise necessary to make an acidic environment. The acid may be selected from the group consisting of acetic acid, hydrochloric acid, nitric acid, phosphoric acid and sulfuric acid.

In the method, the acceptable extraction agent may be selected from the group consisting of lower acetates, lower ketones, lower ether, lower alcohols and benzenes.

The method may further comprise at least a first washing step to wash the organic layer with an acceptable aqueous salt solution. The acceptable aqueous solution may be a solution of a salt or hydroxide selected from the group consisting of ammonium chloride, sodium carbonate, sodium bicarbonate, potassium carbonate, sodium hydroxide, potassium hydroxide, sodium thiosulfate, sodium sulfite and sodium hydrosulfide. The acceptable aqueous salt solution may preferably be a solution of a salt selected from the group consisting of sodium thiosulfate, sodium sulfite and sodium hydrosulfide.

Preferably the aqueous salt or hydroxide solution is at a pH between 5 and 14, more preferably pH 7–14, or pH 6–12, yet more preferably pH 7.5–9.5, most preferably pH 8.3–9.3.

Generally, the preferred pH of the aqueous salt or hydroxide solution is an alkali pH, thus making an aqueous alkali salt or hydroxide solution.

The aqueous alkali solution may be also an alkali hydroxide aqueous solution such as a sodium hydroxide solution or a potassium hydroxide solution.

The method may further comprising a second washing step to wash the organic layer with an acceptable aqueous salt or hydroxide solution. The acceptable aqueous salt or hydroxide solutions of the second wash step is selected from the group consisting of ammonium chloride, sodium carbonate, sodium bicarbonate, potassium carbonate, sodium hydroxide, potassium hydroxide, sodium thiosulfate, sodium sulfite and sodium hydrosulfide. The second washing step may be performed with a solution that is different from the solution used in the first washing step.

The method may further comprise a step to destroy excess oxidation reagent in the organic layer by contacting the organic layer with a metal containing catalyst or a nonmetal catalyst.

The method may further comprise a step of drying the organic layer to form an extract containing terpene trilactones. The dried extract contains more than 50% by weight terpene trilactones, preferably more than 55%, yet more preferably more than 60%.

The method may further comprise a step of recrystallizing the extract containing terpene trilactones to obtain terpene trilactones in higher purity. The recrystallization may be performed with an acceptable solvent or solvent mixture.

The method may further comprise a step of purification by treatment with or filtration over activated charcoal.

The method may further comprise a step of purification by treatment with or filtration over alumina, such as aluminum oxide.

Another embodiment of the subject inventions is a method of isolating terpene trilactones from *Ginkgo biloba* plant material or extract comprising the steps of:
 suspending the plant material or extract in an aqueous solution of an oxidation reagent;
 extracting the terpene trilactones using an acceptable extraction agent;
 separating the organic layer from the aqueous layer;
 washing the organic layer with an acceptable aqueous salt or hydroxide solution; and
 drying the organic layer to form a dried extract containing terpene trilactones, thereby isolating the terpene trilactones.

The parameters of this embodiment may be as discussed above for the previous method. Similarly, any additional steps as discussed above may be present in this embodiment.

This method, as well as the previous method, may further comprise a step of heating or boiling the suspended plant material or extract in aqueous solution for a period of time between 5 minutes and 5 hours.

This method, as well as the previous method, may further comprise a step of adjusting the pH of the suspended plant material or extract in aqueous solution to a range of about pH 4 and pH 6.5.

Yet another embodiment is a method of isolating terpene trilactones from *Ginkgo biloba* plant material or extract comprising the steps of:
 suspending the plant material or extract in an aqueous solution of hydrogen peroxide;
 adjusting the pH of the suspended plant material or extract in aqueous solution to a pH of between 4 and 6.5;
 extracting the terpene trilactones using an acceptable extraction agent;
 separating the organic layer from the aqueous layer;
 washing the organic layer with an aqueous alkaline salt or hydroxide solution;
 drying the organic layer to form a dried extract containing terpene trilactones; and
 recrystallizing the dried extract containing terpene trilactones to obtain terpene trilactones in higher purity
 to thereby isolate the terpene trilactones.

The parameters of this embodiment may be as discussed above for the previous two embodiments. Similarly, any additional steps as discussed above may be present in this embodiment.

In this embodiment, the aqueous solution may contain 0.1% to 30% hydrogen peroxide. The recrystallization may be performed with an acceptable solvent or solvent mixture.

The method may further comprise a step of purification by treatment with or filtration over activated charcoal.

The method may further comprise a step of purification by treatment with or filtration over alumina, such as aluminum oxide.

A further embodiment is a method of isolating terpene trilactones from *Ginkgo biloba* plant material or from an extract comprising the steps of:
 suspending the plant material or extract in water;
 extracting the terpene trilactones using an acceptable extraction agent;
 separating the organic layer from the aqueous layer;
 washing the organic layer with an aqueous alkaline salt or hydroxide solution;
 to thereby isolate the terpene trilactones in the organic layer.

The parameters of this embodiment may be as discussed above for the previous embodiments. Similarly, any additional steps as discussed above may be present in this embodiment.

In this embodiment, the separation may be performed with the addition of sodium chloride to the emulsion containing organic and aqueous layers. The aqueous alkaline salt solution may also be a sodium sulfite solution.

The terpene trilactones from any of the embodiments can be purified by further processing, for example by reversed phase chromatography, to reduce any unwanted ginkgolic acids. For example, chromatography can be performed with silica gel.

The method of isolating and concentrating terpene trilactones (ginkgolides A,B,C,J and bilobalide) from leaves of the tree *Ginkgo biloba* or from pharmaceutical powder produced by extraction of the leaves of *Ginkgo biloba*, for example Egb761, can generally proceed by the following procedures:

(A) Suspend the dried leaves or the pharmaceutical powder 1) in water, or 2) in an aqueous solution containing hydrogen peroxide at a concentration range of 0.1–30%, or 3) in an aqueous solution containing hydrogen peroxide at a concentration range of 0.1–30% and additional 0.1–15% percent of mineral acids like acetic, hydrochloric, nitric, phosphoric or sulfuric acid;

(B) Stir only, stir and heat, or stir and boil the suspension of (A) for a period of time between 5 min to 5 hours;

(C) If necessary, adjust the pH after this treatment to a range of pH 4–6 with alkali hydroxide aqueous solutions such as sodium hydroxide or potassium hydroxide;

(D) Extract the suspension of (B) or (C) with lower acetates, lower ketones, lower ether, lower alcohols or benzenes, separate the organic layer from the aqueous solution;

(E) Wash the organic layer 1) with an aqueous based solution, such as ammonium chloride, sodium carbonate, sodium bicarbonate, potassium carbonate or with alkali hydroxide aqueous solutions such as sodium hydroxide or potassium hydroxide, or 2) with an aqueous solutions such as sodium thiosulfate, sodium sulfite and sodium hydrosulfide or destroy the excess of hydrogen peroxide with metal dust or on metal based catalysts, or both of 1) and 2);

(F) Wash the organic layer with water and/or with an aqueous solution of sodium chloride;

(G) Separate, dehydrate and dry the remaining organic layer, remove solvent and obtain an extract which contains more then 50% terpene trilactones; and (H) Recrystalize the extract from step (G) with a mixture of water/methanol or any other acceptable solvent system to obtain the ginkgolides in high purity.

The parameters and characteristics of each of the embodiments described above are interchangeable when applicable to each other, and are therefore not repeated. Thus, for example, any parameter or characteristic of the first embodiment may be employed in the other embodiments of the invention.

Experimental Details

In the following examples, the invention is described in details. All examples produce an extract, which contains between 55% and 75% of terpene trilactones before recrystallization. After recrystallization with a water/methanol mixture, the terpene trilactones were obtained in high purity. Besides resulting in a higher purity and higher yields, the disclosed method is performed in a decreases time for the extraction process thus helping to save energy. Also, in this method, the water and organic layers are simple to separate, the method maintains the natural distribution of the terpene trilactones levels, and gives high recovery of the terpene trilactones.

EXAMPLE 1

250 g of dried leaves from *Ginkgo biloba* was suspended in 2 L 5% hydrogen peroxide aqueous solution and boiled for 1 h. The suspension was hot filtrated through a Büchner funnel without filter paper. The remaining leaf fibers were washed with 2×100 mL water by vaccum filtration. The filtrate was then extracted first with 250 mL ethyl acetate, then a second time with 125 mL ethyl acetate. The organic layers were combined followed by the washing procedure. First washing 3× (200 mL, 100 mL, 100 mL) with a saturated aqueous solution of sodium bicabonate, second 2× (200 mL, 100 mL) with a saturated aqueous solution of sodium sulfite and third with 100 mL water and then with 100 mL sodium chloride solution (80%). After this washing procedure the organic layer was dried over sodium sulfate and the solvent removed. The resulting 830 mg powder contained 52% terpene trilactone, quantified by NMR. The ratio between the terpene trilactones BB:GA:GB:GC:GJ with 4.8 (57%):1.4 (16%):1.0 (12%):0.9 (11%):0.3 (4%) followed the natural distribution pattern.

EXAMPLE 2

250 g of dried leaves from *Ginkgo biloba* was suspended in 2.5 L 5% hydrogen peroxide aqueous solution and boiled for 1 h. The suspension was hot filtrated through a Büchner funnel without filter paper. The remaining leaf fibers were washed with 2×100 mL water by vacuum filtration. The pH of the filtrate was adjusted to 4.5 by addition of an 1 N aqueous solution of sodium hydroxide. After this treatment, the water solution was extracted first with 300 mL of a 2:1 mixture of ethylacetate and diethylether and second with 150 mL of the same mixture. The organic layers were combined followed by the washing procedure. First washing 3× (200 mL, 100 mL, 100 mL) with a saturated aqueous solution of sodium bicarbonate, second 2× (200 mL, 100 mL) with a saturated aqueous solution of sodium thiosulfate and third with 100 mL water and finally with 100 mL sodium chloride solution (80%). After this washing procedure the organic layer was dried over sodium sulfate and the solvent removed. The resulting powder contained 50% terpene trilactones, quantified by NMR.

EXAMPLE 3

25 g of pharmaceutical extract powder from *Ginkgo biloba* was suspended in 500 mL 5% hydrogen peroxide aqueous solution and boiled for 1 h. After cooling to room temperature, the suspension was filtrated through a Büchner funnel without filter paper. Afterwards, the filtrate was extracted first with 250 mL ethyl acetate, then a second time with 125 mL ethyl acetate. After separation from the water layer, the organic layers were combined followed by the washing procedure. First washing 3× (200 mL, 100 mL, 100 mL) with a saturated aqueous solution of sodium bicabonate, second 2× (200 mL, 100 mL) with a saturated aqueous solution of sodium sulfite and third with 100 mL water and finally with 100 mL sodium chloride solution (80%). After this washing procedure the organic layer was dried over sodium sulfate and the solvent removed. The resulting 3.4 g powder contained 55% terpene trilactone, quantified by NMR.

EXAMPLE 4

25 g of pharmaceutical extract powder from *Ginkgo biloba* was suspended in a 500 mL 5% hydrogen peroxide aqueous solution and boiled for 30 min. After cooling to room temperature, the suspension was filtrated through a büchner funnel without filter paper. The filtrate was extracted first with 250 mL ethyl acetate, then a second time with 125 mL ethyl acetate. The organic layers were combined followed by washing 3× with a saturate aqueous solution of sodium sulfite (200 mL, 100 mL, 50, mL) afterwards with 100 mL water and finally with 100 mL sodium chloride solution (80%). After this washing procedure the organic layer was dried over sodium sulfate and the solvent was removed. The resulting 2.8 g contained 60% terpene trilactones, quantified by NMR.

EXAMPLE 5

25 g of pharmaceutical extract powder from *Ginkgo biloba* was suspended in 500 mL water and boiled for 30 min. After cooling to room temperature, this suspension was extracted with ethyl acetate ($1^{st}$ with 250 mL, $2^{nd}$ with 50 mL). Without hydrogen peroxide a emulsion was obtained, but the layers of this emulsion separated slower than the procedure using hydrogen peroxide. After filtration and adding sodium chloride, the layers separated. The organic layers were combined followed by washing 3× with a saturated aqueous solution of sodium sulfite (200 mL, 100 mL, 50 mL), afterwards washed with 100 mL water and finally with 100 mL sodium chloride solution (80%). After this washing procedure the organic layer was dried over sodium sulfate and the solvent was removed. The resulting 3.0 g powder contained 53% terpene trilactone, quantified by NMR.

EXAMPLE 6

25 g of pharmaceutical extract powder from *Ginkgo biloba* was suspended in 500 mL 5% hydrogen peroxide aqueous solution, containing additional 1% of sulfuric acid and boiled for 15 min. The suspension was hot filtrated through a büchner funnel without filter paper. After cooling to room temperature, the filtrate was extracted first with 250 mL ethyl acetate, then a second time with 125 mL ethyl acetate. After separation from the water layer, the organic layers were combined followed by the washing procedure. First washing 3× (200 mL, 100 mL, 100 mL) with a saturated aqueous solution of sodium bicabonate, second 2× (200 mL, 100 mL) with a saturated aqueous solution of sodium sulfite and third with 100 mL water and then with 100 mL sodium chloride solution (80%). After this washing procedure the organic layer was dried over sodium sulfate and the solvent removed. The resulting 1.9 g powder contained 70% terpene trilactone, quantified by NMR.

EXAMPLE 7

25 g of pharmaceutical extract powder from *Ginkgo biloba* was suspended in 500 mL 5% hydrogen peroxide aqueous solution, containing additional 1% of acetic acid and boiled for 30 min. After cooling to room temperature, the suspension was passed through a büchner funnel without filter paper. The filtrate was extracted first with 250 mL ethyl acetate, then a second time with 125 mL ethyl acetate. The organic layers were combined followed by the washing procedure. First washing 3× (200 mL, 100 mL, 100 mL) with a saturated aqueous solution of sodium bicabonate, second 2× (200 mL, 100 mL) with a saturated aqueous solution of sodium thiosulfite. Afterwards washing with 100 mL water and then with 100 mL sodium chloride solution (80%) for removing base and salt excess. After this washing procedure the organic layer was dried over sodium sulfate and the solvent was removed. The resulting 2.8 g powder contained 59% terpene trilactone, quantified by NMR.

EXAMPLE 8

25 g of pharmaceutical extract powder from *Ginkgo biloba* was suspended in 500 mL 5% hydrogen peroxide aqueous solution and boiled for 1 h. After cooling to room temperature, the suspension was filtrated through a büchner funnel without filter paper. The pH of the filtrate was adjusted to 5–6 by addition of 1 N aqueous solution of sodium hydroxide. After this treatment, the water solution was extracted first with 250 mL ethyl acetate, then a second time with 125 mL ethyl acetate. After separation from the water layer, the organic layers were combined followed by the washing procedure. First washing 3× (200 mL, 100 mL, 100 mL) with a saturated aqueous solution of sodium bicabonate, second 2× (200 mL, 100 mL) with a saturated aqueous solution of sodium sulfite and third with 100 mL water and then with 100 mL sodium chloride solution (80%). After this washing procedure the organic layer was dried over sodium sulfate and the solvent removed. The resulting 2.73 g powder contained 60% terpene trilactone, quantified by NMR.

EXAMPLE 9

Some leaf extracts possessed a significant amount of the generally undesired ginkgolic acids.

n = 7–9
Ginkgolic acids

The ginkgolic acids were removed by reversed-phase chromatography. (Chang, M.) The content of the two predominant ginkgolic acids found in *G. biloba* leaves were measured by HPLC using PDA detection; in each case measured, the individual ginkgolic acids were present in amounts lower than the limit of quantitation (10 ppm).

General Experimental Procedures.

$^1$H and $^{13}$C Spectra were acquired on either a 300 or 400 MHz Bruker NMR using standard pulse sequences and parameters; further details are described below. Negative ion FABMS data were determined using a JMS-HX110 Tandem Mass spectrometer (JEOL, Tokyo Japan) instrument using Xe beam (6 kV) with a 10 kV acceleration voltage and m-nitrobenzyl alcohol (NBA) matrix. Analytical HPLC measurements were performed on a Waters 996 PDA system with a Millenium™ Version 2.15.01 software package. Concentration graphs and linear regression were determined with Microsoft Excel® 2000. Semipreparative HPLC isolations were achieved on a LC-908 (Japan Analytical Industry Co., Ltd.) instrument equipped with internal refractive index and ultraviolet detectors and a recorder.

Extract Material.

Bioginkgo™ 27/7 brand *G. biloba* extract was generously donated by Pharmanex (Provo, Utah).

Plant Material.

The leaves were collected from a female *G. biloba* tree in Morningside Park, New York, N.Y. Yellow leaves were collected (having fallen to the ground) in November 2000 and green leaves were collected in June 2001. They were frozen in liquid nitrogen, crushed and lyophilized until constant weight. The moisture content was 59% in the yellow leaves and 73% in green leaves. Further samples of these leaves are stored in our laboratory.

General Extraction of TTLs.

Figure 6:
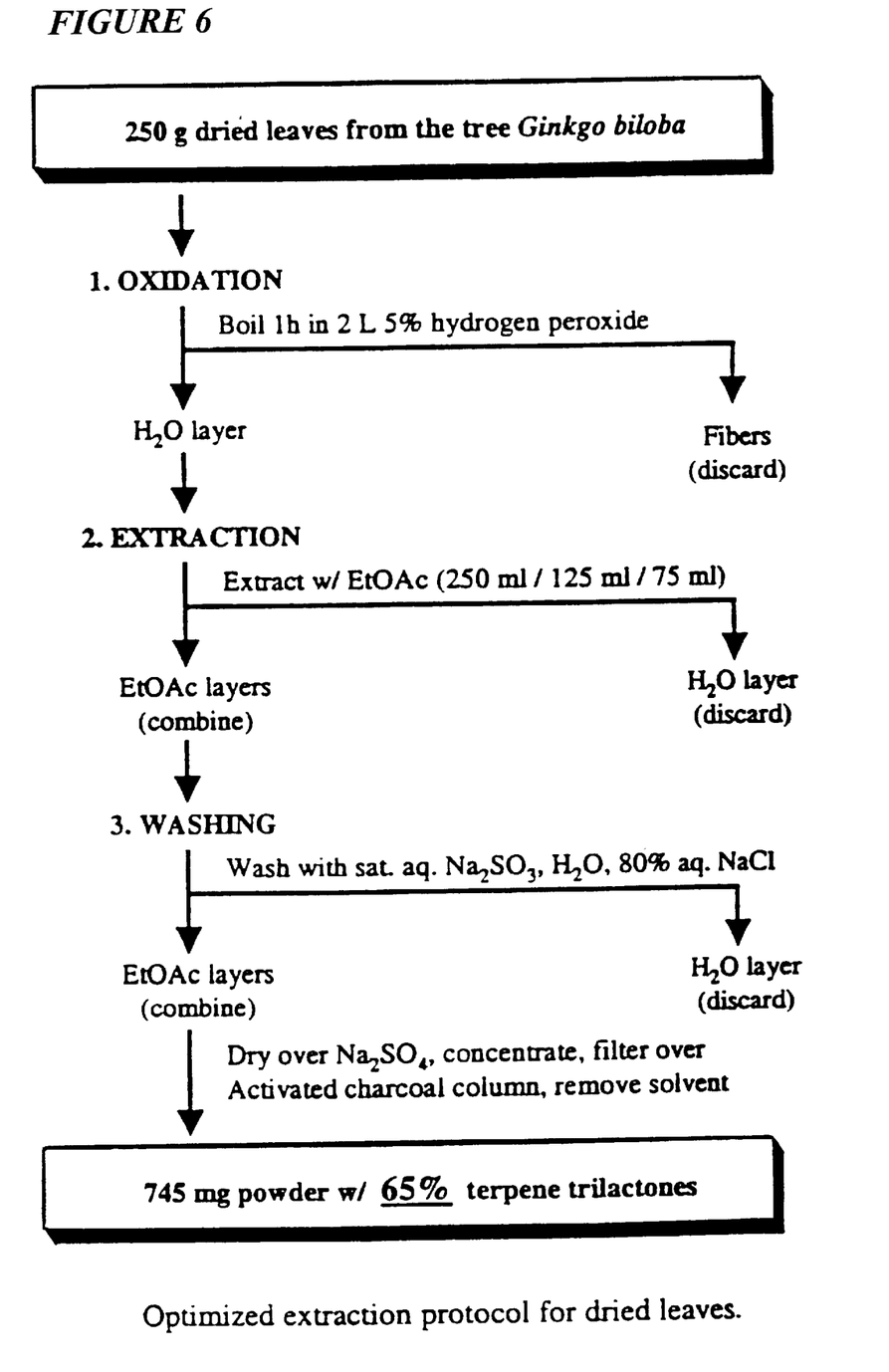
FIG. 6 Optimized extraction protocol for dried leaves.

Bioginkgo™ 27/7 extract (25 g) or lyophilized leaves (250 g) were boiled for 1 h in 0.5 L (extract) or 2 L (leaves) aqueous 5% aq. $H_2O_2$ (or other oxidation reagents in water). After passing (extract=RT, leaves=boiling) through a Buchner funnel w/o filter paper, the remaining solution was extracted up to 3 times w/EtOAc (250/125/75 mL). The organic layer was washed w/sat. aq. salt solution ($NaHCO_3$/$Na_2S_2O_3$ $NaHCO_3$/$Na_2SO_3$ or $Na_2SO_3$) followed by water and 80% aq. NaCl. (saturated aq. solution diluted to 80%). After drying over $Na_2SO_4$, solvent was removed to yield an amorphous yellow powder with 50–60% TTL content. See, FIG. 6.

For further purification these extracts were dissolved in EtOAc and passed through an activated charcoal column. Concentration gave an off-white amorphous powder w/60–70% content of TTLs. A more rigorous procedure involved dissolving the extracts in methanol, adding activated charcoal, and filtering over Celite 545.

TLC Analysis of TTLs.

Thin layer chromatography of TTLs was performed as previously reported. (van Beek, 1993)

HPLC Separation of TTLs.

A 1×25 cm 5 m YMC ODS-AM column with a 1 mL/min $H_2O$:MeOH:THF (7:2:1) solvent system was used to separate the TTLs; monitoring was performed with a refractive index detector. (O'Reilly)

Removal of Ginkgolic Acids.

Ginkgolic acids were removed from the extracts by reversed-phase chromatography using polymeric resins such as Dianon® HP-20(Chang, M.) or Amberlite® XAD-16 with a step gradient of increasing methanol (30–90%) in water. TTL containing fractions (40–80%, as determined by NMR or TLC) were combined and the solvent was removed to afford the final products. WP C18 silica was also employed (twice) with aq. 60% methanol successfully to remove ginkgolic acids.

Extraction of Ginkgolic Acids.

Standards were isolated from hexane-extracted G. biloba leaves that were subjected to chromatography with silica gel (1% MeOH in $CHCl_3$), RP-18 silica gel (0–100% MeOH, retaining the 100% MeOH fraction), and semi-preparative HPLC (1×25 cm 5 m YMC ODS-AM column, $H_2O$:MeOH:AcOH (100:10:1) solvent system, monitored at 215 hm). Spectroscopic analyses of these compounds ($^1H$ NMR, $^{13}C$ NMR, and negative mode FABMS) provided results similar to those previously reported. (Itokawa, H.)

Quantitation of Ginkgolic Acids.

Ginkgolic acid standards (3, 5, 25, 50, 250 hg) in MeOH (5 mL) were injected onto a 4.6×150 mm Phenomenex® Luna 5 m C18(2) column with 0.1% TFA in MeCN solvent system (flow rate=1 mL/min) and detection at 215 hm; concentration graphs showing good linearity ($R^2 \geq 0.99$). Multiple injections determined the level of quantitation to be 10 ppm. Samples were prepared by dissolving 1–2 mg of extract in 100 mL MeOH; 20 mL injections were then analyzed in a similar fashion.

Discussion

An efficient and rapid protocol has been developed for extracting ginkgolides and bilobalide (terpene trilactones, TTLs) from *Ginkgo biloba* leaves. The procedure takes advantage of the extraordinary stability, despite the presence of multiple oxygen functions, of the TTL structure to a variety of chemical treatments, especially oxidation. The protocol involves boiling the aqueous extract of leaves with dilute hydrogen peroxide, extraction with ethyl acetate, washing with basic solutions, and charcoal filtration to yield off-white powder, TTL content 60–70%. Presumably the hydrogen peroxide treatment degrades undesired leaf constituents that lead to intense emulsification during extractions. Further reversed phase chromatography of the extracts with polymeric resins removes the undesirable ginkgolic acids to amounts less than 10 ppm. The extracts are suited for pure TTL preparation, enrichment of TTL content in nutraceuticals, and preparations of low-flavonoid/high-TTL controls in medicinal studies.

EGb 761, (Polich, J.) a standardized extract of the leaves, contains 5–7% ginkgolides (Kennedy, D. O.; DeFeudis, F. V.) and bilobalide (BB) (Braquet P.) (terpene trilactones, TTLs) along with 22–24% flavonoids and less than 5 ppm ginkgolic acids (also known as anacardic acids).(Polich, J.) This limit was imposed because alkylphenols such as ginkgolic acids have been reported to induce contact dermatitis (Ishii, S.; Kato, K.); cytotoxicity was also reported for these compounds. (Bito, H.)

An efficient and economical extraction of TTLs is essential to secure the amounts of materials required for bioorganic and other studies. In contrast to conventional isolation procedures, which are tedious and lengthy, (O'Reilly, J.) the method described concentrates the TTLs in the leaves (ca. 0.2%) to 70% in three rapid steps of oxidation, extraction and washing. The clear advantage is that, at least at the laboratory scale, the extraction is shortened from several days to one day because of minimal emulsion formation in the EtOAc extraction process, and that only a single common organic solvent is used. The resulting extracts are ideal as starting material for pure TTL preparation from leaves, for enriching TTL content in dietary supplements, and as low-flavonoid/high-TTL controls in medicinal studies.

Figure 1:
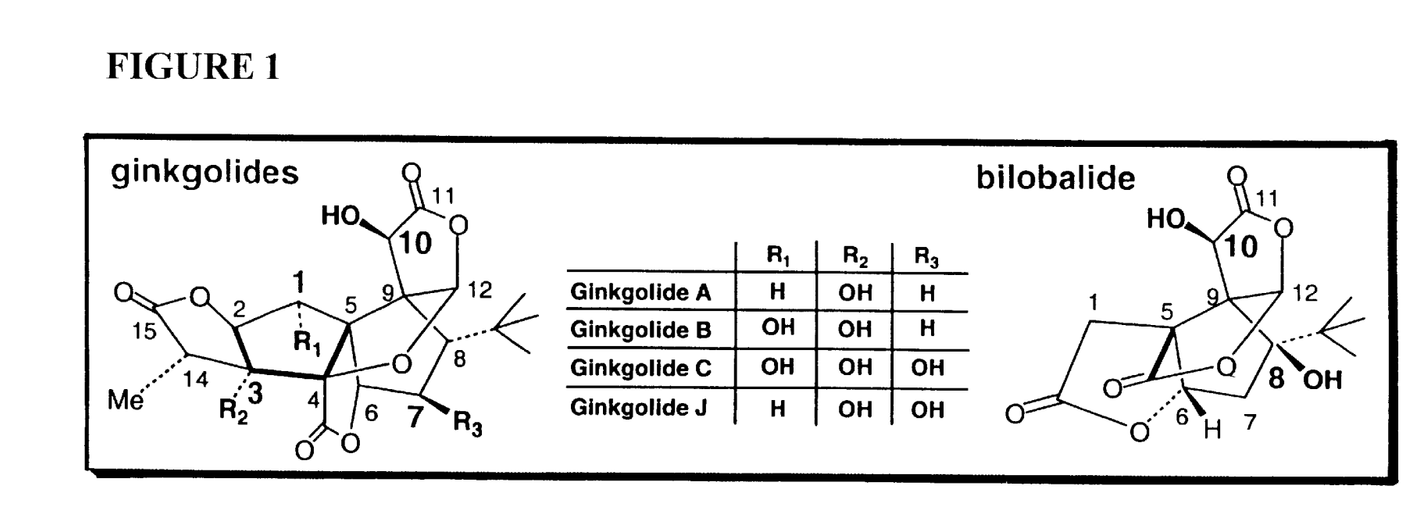
FIG. 1 Bilobalide and Ginkgolide A, B, C, J and M.
Figure 2:
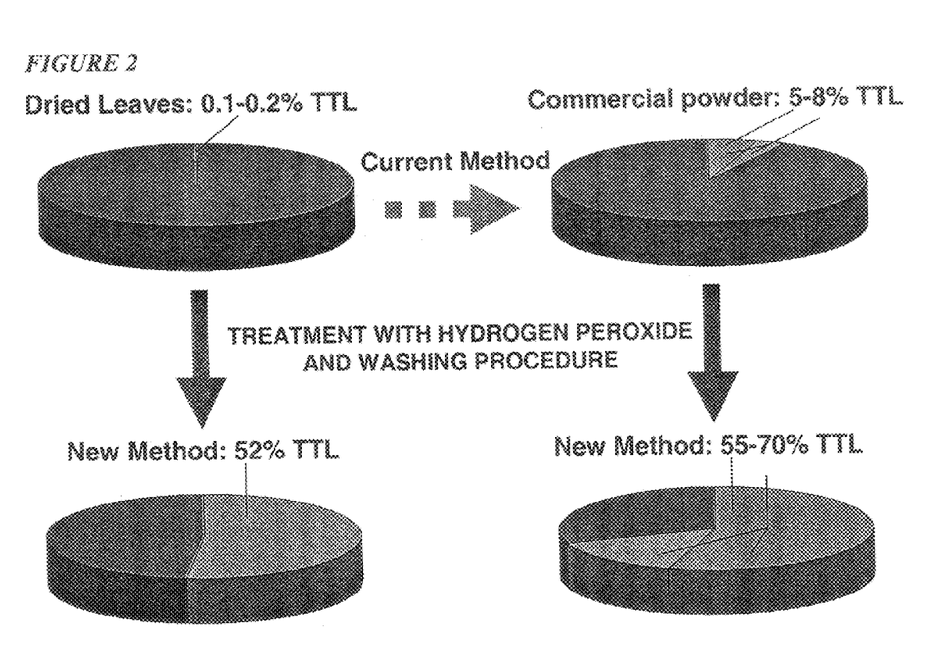
FIG. 2 Summary of disclosed isolation method of terpene trilactones from *Ginkgo biloba* leaves.
Figure 3:
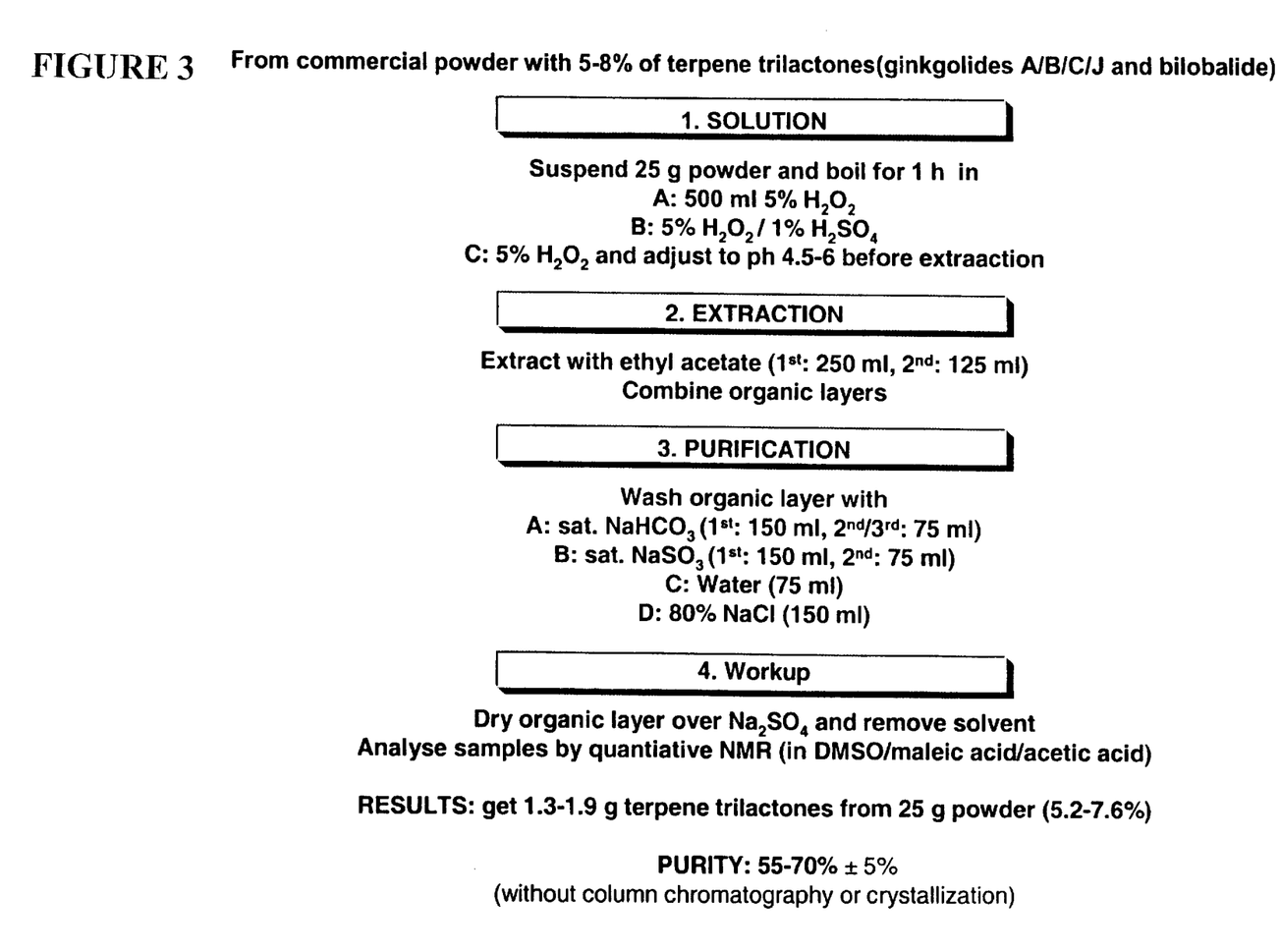
FIG. 3 One embodiment of the disclosed isolation method of terpene trilactones from *Ginkgo biloba* leaves. Step 1. can be performed with either of A, B, or C. Step 3. can be performed with C and D, and either of A or B. Step 3. can also be performed with C, and D and both of A and B.
Figure 4:
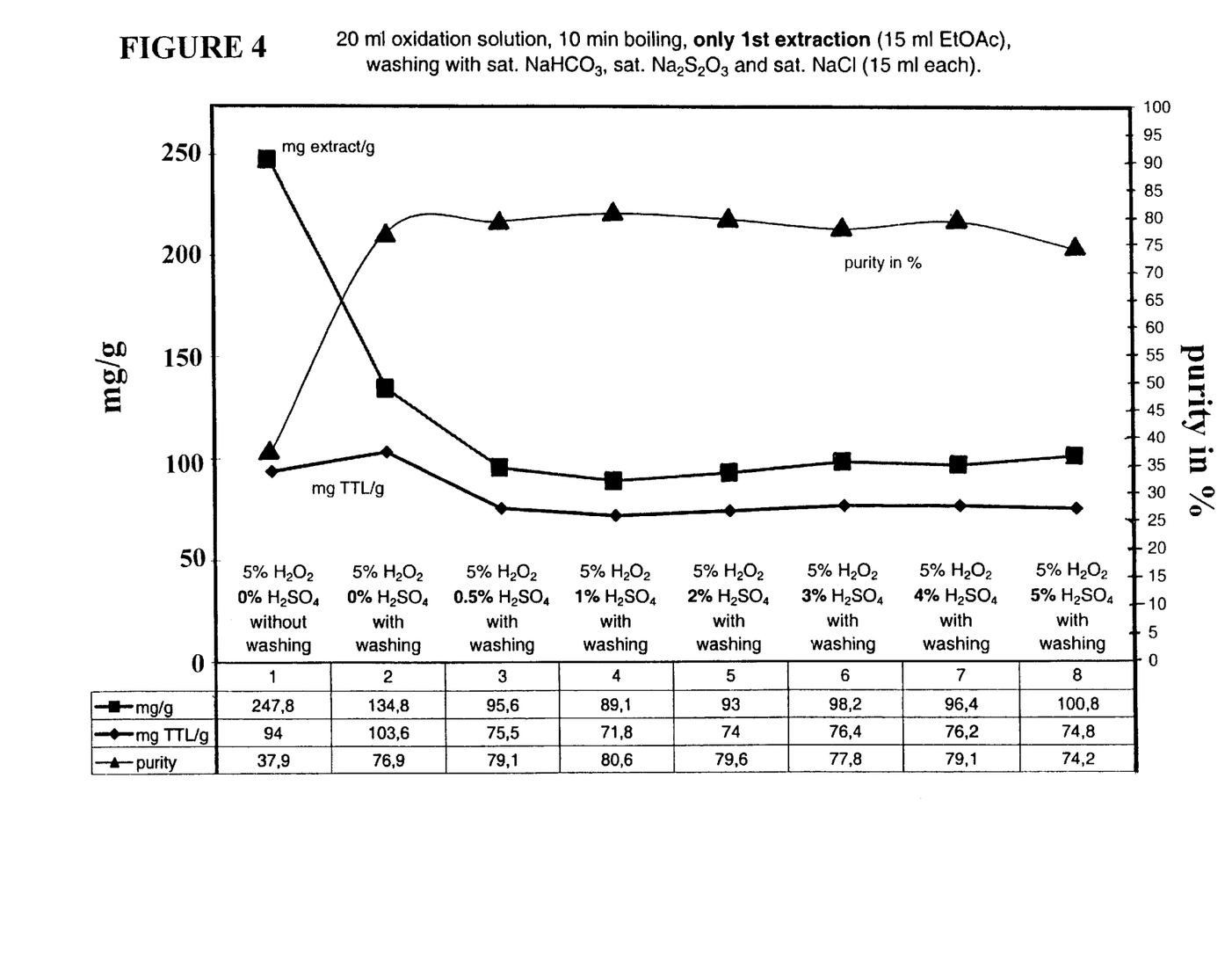
FIG. 4 Isolation of terpene trilactones from *Ginkgo biloba* leaves 0–10% $H_2O_2$ and 0–5% $H_2SO_4$.
Figure 5:
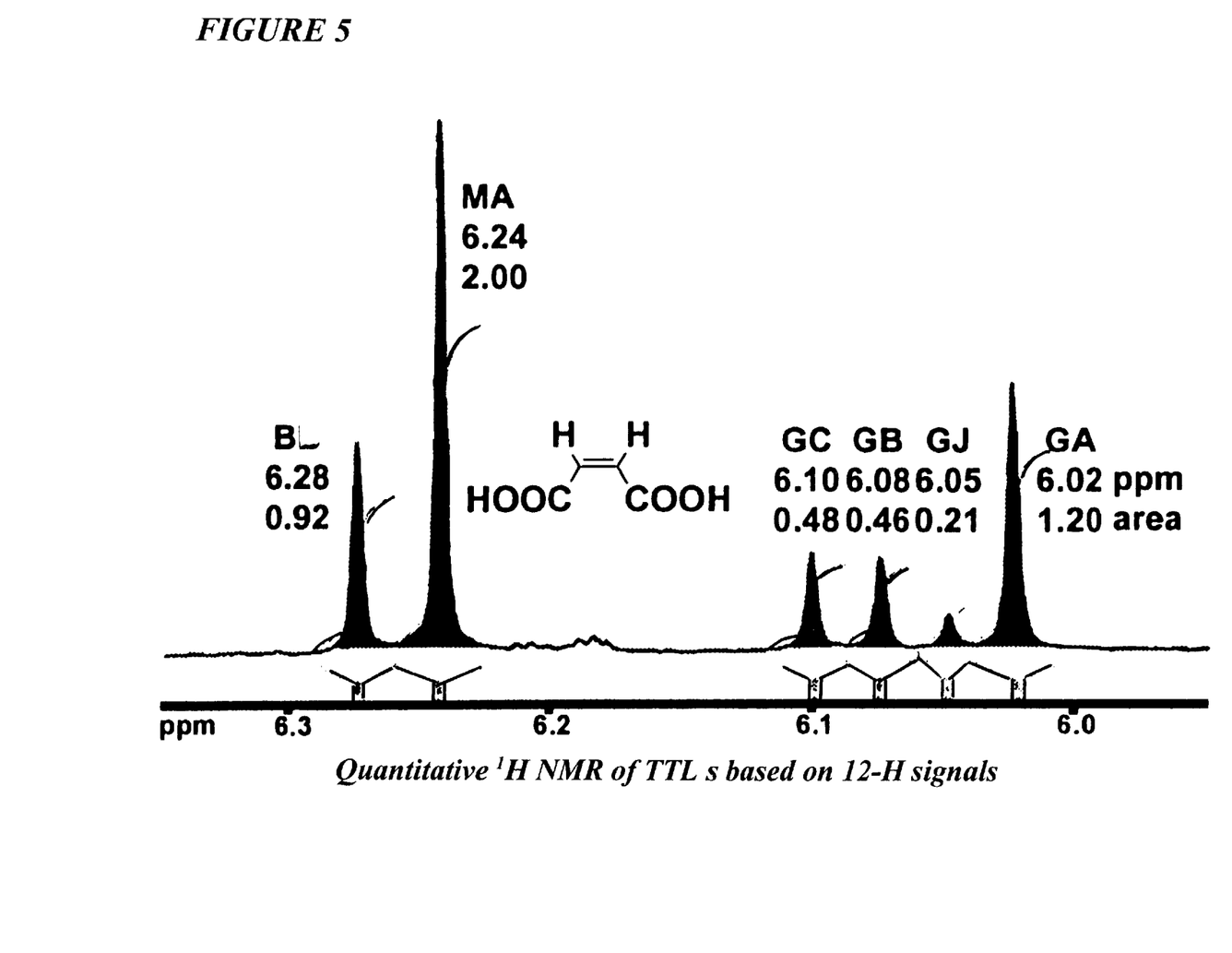
FIG. 5 Quantitative NMR of TTLs based on 12-H signal (Bruker 400 MHz).

Quantitative NMR analyzed the TTLs in the extracts (van Beek, 1993) by taking advantage of the 12-H signals, which in all TTLs appear as well separated singlets. Using the two olefinic protons of maleic acid as an internal standard, DMSO was used instead of the solvent mixture originally described, and a small amount of acetic acid was added to avoid peak shifts in the 12-H region of the spectrum. See, FIG. 5.

During structural studies of ginkgolides it was found that they are cage compounds of extraordinary stability despite the presence of many oxygen functions (Maruyama, M.). They are unaffected by boiling in conc. nitric acid, alkali fusion of GA merely results in expulsion of C-10/C-11 to generate a hemiacetal, while treatment of GA in conc. sulfuric acid with sodium dichromate simply converted the hydroxy lactone to its oxolactone. Utilizing this extraordinary stability, we investigated various oxidation conditions and subsequent workup to destroy/remove components other than TTLs in the leaves.

The process is composed of boiling the TTL-containing material in water with a oxidizing agent, filtering, extracting the filtrate with ethyl acetate, washing the organic phase with basic solutions, and solvent removal. These extraction processes were first optimized with a G. biloba extract (Pharmanex Bioginkgo™ 27/7, 27% flavonoids/7% TTLs) and then applied to leaves. Several oxidizing reagents such as hydrogen peroxide, 3-chloroperbenzoic acid (MCPBA) and $MnO_2$ were tested for extraction suitability of TTLs from Bioginkgo™ powder. The yields and percent contents of TTLs of the extracts boiled with $H_2O_2$, MCPBA and pure water were similar, i.e., 55% TTLs. There was a significant decrease in the yield after $MnO_2$ treatment due to destruction of BB (which is much less stable than the ginkgolides) but the amounts of ginkgolides also decreased, probably due to absorption onto solid $MnO_2$. Further investigations were focused on $H_2O_2$ as it was the only oxidizing agent that provided distinct layer separation during extraction, while the other agents resulted in emulsions with lower recovery of TTLs; it is likely that the $H_2O_2$ treatment destroys the ingredient(s) leading to tenacious emulsification in the step involving extraction into the organic layer (ethyl acetate).

The concentration of $H_2O_2$ was varied to determine the optimal concentration. With washing, the total amount of extract decreased with higher percentages of $H_2O_2$, but without washings the opposite was observed. Good separation of layers was found for 5% and 10% $H_2O_2$, whereas 1% $H_2O_2$ gave an emulsion and 3% $H_2O_2$ required more time for layer separation. The highest recoveries of TTLs with washing were found for 3% and 5% $H_2O_2$. After extraction, $H_2O_2$ was detected in the organic layer (by the color change on filter paper impregnated with potassium iodide) and in the case of 10% $H_2O_2$, the excess peroxide gave rise to an exothermic reaction upon workup. Therefore 5% $H_2O_2$ was used in all further investigations. With respect to the boiling time, 1 h. was found to be optimal.

The Bioginkgo™ powder as well as leaves gave rise to acidic water (pH 3) after boiling. Since peroxide oxidation should work better under acidic conditions, oxidation with 5% $H_2O_2$ and additional 1% of several acids were tested. The results were either no change or decreased recovery of TTLs. It was thus concluded that use of aqueous $H_2O_2$ without additional acid was optimal.

After boiling with peroxide, all mixtures were extracted three times with EtOAc. With respect to the number of extraction, three turned out to be sufficient. For leaf extractions, a precipitate present in the organic layer had to be removed by filtration. Washing the EtOAc layer with basic solutions was critical for high TTL content. Base was used to neutralize organic acids and to destroy peroxide excess, but the lactones in the TTLs could open under such treatment, resulting in increased water solubility. For GB it was reported that lactones start opening at pH 6.5. (Zekri, O) As expected, aqueous $Na_2CO_3$ (pH 10.4) and NaSH (pH 10.8) resulted in lower recovery yields of TTLs, with BB and ginkgolide C (GC) no longer detected in the extract. However, washing with saturated solutions of $NaHCO_3$ and $Na_2S_2O_3$ (both pH 8.3) and $Na_2SO_3$ (pH 9.3) led to consistent extraction yields and high TTL content. Further workup yielded extracts containing 50–70% TTLs. In contrast to basic solutions, use of aqueous $NH_4Cl$ (pH 5) was not effective in removing impurities.

Since the lactones of TTLs are closed at pH 3, the presence of any TTL in the discarded aqueous layer after washing with $Na_2SO_3$ (pH 9.3) was tested after acidification of the combined water layers with 1 N HCl; no TTLs were detected by TLC. Using the same procedure for the water layers after washing with $Na_2CO_3$ (pH 10.4), GC and decomposition products of BB were found.

Figure 7A:
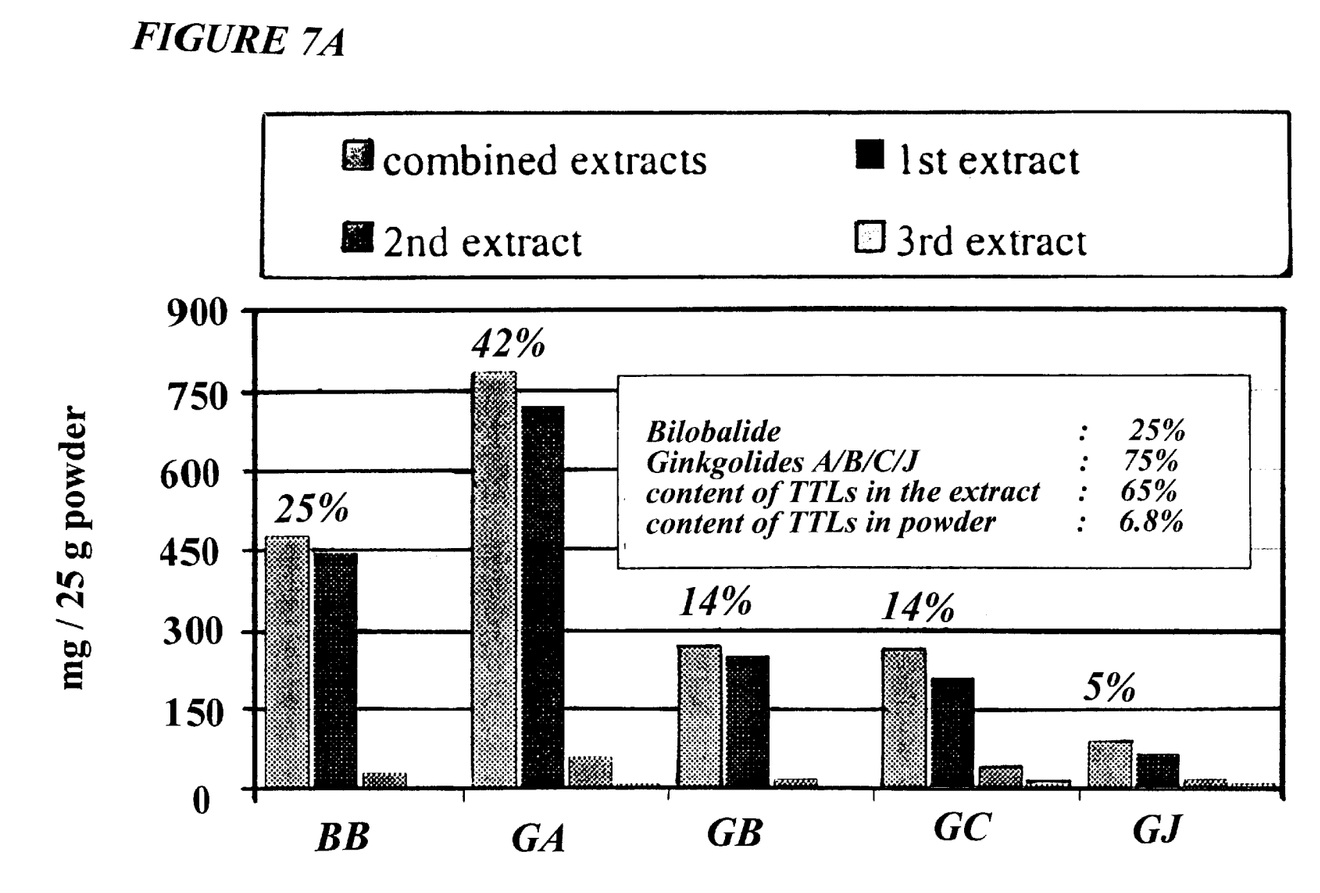

A typical extract prepared from Bioginkgo™ 27/7 is shown in FIG. 7A. Small quantities of pure TTLs were obtained from such extracts with semi-preparative reversed-phase HPLC (Teng, B. P.); larger quantities can be purified by a number of different procedures. (Teng, B. P.; van Beek 1997)

Figure 7B:
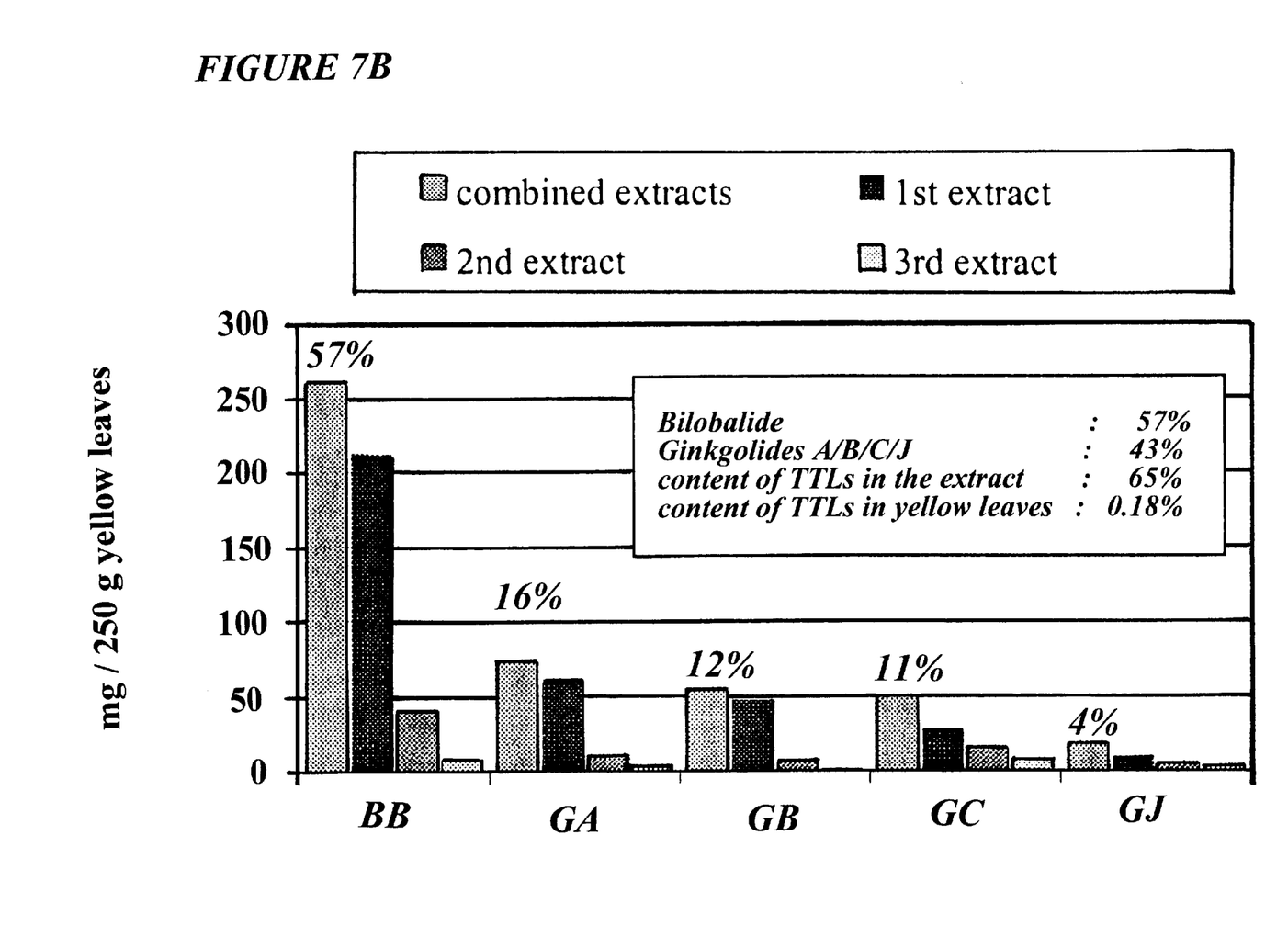
Figure 7C:
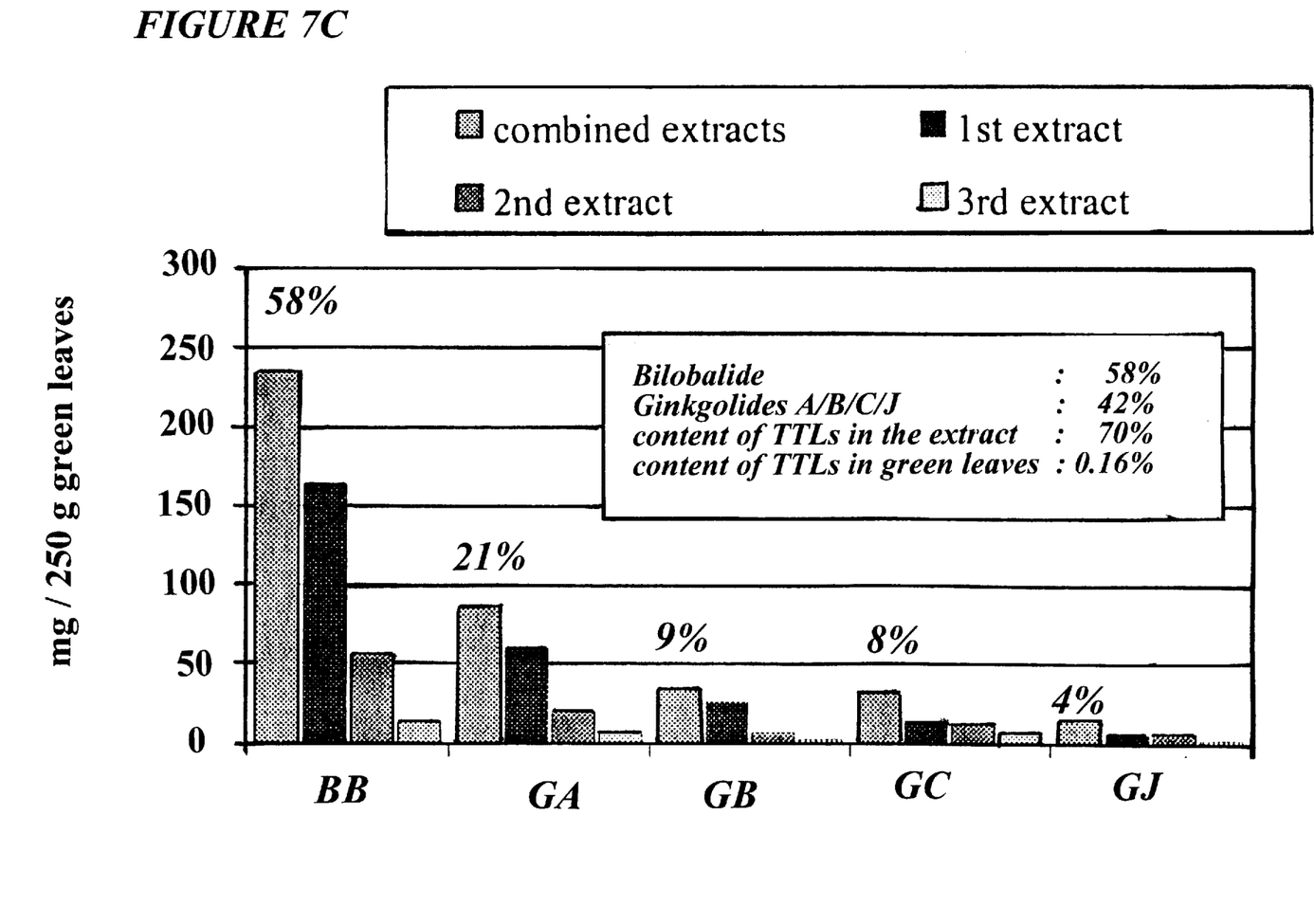

After optimization, the protocol was applied to dried leaves. The total TTL contents were similar for the treated Bioginkgo™ 27/7 powder (65%), the yellow leaves (65%) and the green leaves (70%) (FIG. 7).

The content of TTLs in leaves depends on seasons and other factors such as tree age. (Laurain, D.) As described for leaves and for EGb761 (26% flavonoids, 6% TTL), BB was always the major component of the TTL content (ca. 50%). (van Beek, 1992; Sticher, O) The procedures described led to minimal BB destruction, high recovery yield and maintained a natural distribution pattern.

REFERENCES

Bito, H.; Nakamura, M.; Honda, Z.; Izumi, T.; Iwatsubo, T.; Seyama, Y.; Oguram A.; Kudo, Y.; Shimizu, T. *Neuron,* 1992, 9, 285–294.

Braquet P.; Etienne A.; Touvay C.; Bourgain R. H.; Lefort J.; Vargaftig B. *Lancet* 1985, 1, 1501.

Chang, M.; Yu, Z; Cooper, R.; Zhang, D. C. PCT Int. Appl. WO 99/26643, Jun. 3, 1999.

Clark, G. D.; Bazan, N. G.; Zorumski, C. F. *Nature,* 1994, 367, 175–179.

DeFeudis, F. V. *Ginkgo biloba extract (Egb 761): From Chemistry to the Clinic;* Ullstein Medical: Wiesbaden, 1998.

Ishii, S.; Shimizu, T. *Prog. Lipid Res.* 2000, 39, 41–82.

Itokawa, H.; Totsuka, N.; Nakahara, K.; Takeya, K.; Lepoitteven, J. -P.; Asakawa, Y. *Chem. Pharm. Bull.* 1987, 35, 3016–3020.

Kennedy, D. O.; Scholey, A. B.; Wesnes, K. A. *Psychopharmacology* 2000, 151, 416–423.

Laurain, D. In *Med. Aromat. Plants—Ind. Profiles,* Vol. 12 (*Ginkgo biloba*); van Beek, T. A. Ed.; Harwood: Amsterdam, 2000; pp. 63–77.

Maruyama, M.; Terahara, A.; Nakadaira, Y.; Woods, M. C.; Takagi, Y.; Nakanishi, K. *Tet. Lett.* 1967, 4, 315–320; see also Nakanishi, K. *Pure Appl. Chem.* 1967, 14, 89–113.

O'Reilly, J. In *Med. Aromat. Plants—Ind. Profiles,* Vol. 12 (*Ginkgo biloba*); van Beek, T. A. Ed.; Harwood: Amsterdam, 2000; pp. 99–108.

Polich, J.; Gloria, R. *Hum. Psychopharmacol. Clin. Exp.* 2001, 16, 409–416.

Sticher, O. *Planta Med.* 1993, 59, 2–11.

Teng, B. P. In *Ginkgolides—Chemistry, Biology, Pharmacology and Clinical Perspectives;* Braquet, P. Ed.; J. R. Prous Science Publishers: Barcelona, 1988; pp. 37–48.

van Beek, T. A.; Lelyveld, G. P. *Planta Med.* 1992, 58, 413–416.

van Beek, T. A.; Lelyveld, G. P. *Phytochem. Anal.* 1993, 4, 109–114.

van Beek, T. A.; Lelyveld, G. P. *J. Nat. Prod.* 1997, 60, 735–738.

Zekri, O.; Boudeville; Genay, Perly; Braquet; Jouenne; Burgot. *Anal. Chem.* 1996, 68, 2598–2604.

What is claimed is:

1. A method of isolating terpene trilactones from *Ginkgo biloba* plant material or extract comprising the steps of:
    suspending the plant material or extract in the presence of an oxidation reagent,
    extracting the terpene trilactones using an acceptable extraction agent, and
    separating the organic layer from the aqueous layer to thereby isolate the terpene trilactones in the organic layer.

2. The method of claim 1, wherein the oxidation reagent is in aqueous solution.

3. The method of claim 1, wherein the oxidation reagent is hydrogen peroxide.

4. The method of claim 2, wherein the aqueous solution contains 0.1% to 50% oxidation reagent.

5. The method of claim 2, wherein the aqueous solution further comprises an acid.

6. The method of claim 5, wherein the aqueous solution contains 0.1% to 15% acid.

7. The method of claim 5, wherein the acid is selected from the group consisting of acetic acid, hydrochloric acid, nitric acid, phosphoric acid and sulfuric acid.

8. The method of claim 1, wherein the acceptable extraction agent is selected from the group consisting of lower acetates, lower ketones, lower ether, lower alcohols and benzenes.

9. The method of claim 1, further comprising at least a first washing step to wash the organic layer with an acceptable aqueous salt or hydroxide solution.

10. The method of claim 9, wherein the acceptable aqueous solution is a solution of a salt or hydroxide selected from the group consisting of ammonium chloride, sodium carbonate, sodium bicarbonate, potassium carbonate, sodium hydroxide, potassium hydroxide, sodium thiosulfate, sodium sulfite and sodium hydrosulfide.

11. The method of claim 10, wherein the acceptable aqueous salt or hydroxide solution is a solution of a salt selected from the group consisting of sodium thiosulfate, sodium sulfite and sodium hydrosulfide.

12. The method of claim 9, wherein the acceptable aqueous salt solution is an aqueous alkali salt solution.

13. The method of claim 9, wherein the aqueous alkali salt solution has a pH of between about 7.5 and 9.5.

14. The method of claim 12, wherein the aqueous alkali solution is an aqueous alkali hydroxide solution selected from the group consisting of a sodium hydroxide solution and a potassium hydroxide solution.

15. The method of claim 9, further comprising a second washing step to wash the organic layer with an acceptable aqueous salt or hydroxide solution.

16. The method of claim 15, wherein the acceptable aqueous salt or hydroxide solutions of the second wash step is selected from the group consisting of ammonium chloride, sodium carbonate, sodium bicarbonate, potassium carbonate, sodium hydroxide, potassium hydroxide, sodium thiosulfate, sodium sulfite and sodium hydrosulfide.

17. The method of claim 15, wherein the second washing step is performed with a solution that is different from the solution used in the first washing step.

18. The method of claim 1, further comprising a step to destroy excess oxidation reagent in the organic layer by contacting the organic layer with a metal or a nonmetal catalyst.

19. The method of claim 1, further comprising a step of drying the organic layer to form an extract containing terpene trilactones.

20. The method of claim 19, wherein the extract contains more than 50% by weight terpene trilactones.

21. The method of claim 19, further comprising a step of recrystallizing the extract containing terpene trilactones to obtain terpene trilactones in higher purity.

22. A method of isolating terpene trilactones from *Ginkgo biloba* plant material or extract comprising the steps of:
   suspending the plant material or extract in an aqueous solution of an oxidation reagent;
   extracting the terpene trilactones using an acceptable extraction agent;
   separating the organic layer from the aqueous layer;
   washing the organic layer with an acceptable aqueous salt or hydroxide solution; and
   drying the organic layer to form a dried extract containing terpene trilactones, thereby isolating the terpene trilactones.

23. The method of claim 22, further comprising a step of heating or boiling the suspended plant material or extract in aqueous solution for a period of time between 5 minutes and 5 hours.

24. The method of claim 22, further comprising a step of adjusting the pH of the suspended plant material or extract in aqueous solution to a range of about pH 4 and pH 6.5.

25. The method of claim 22, further comprising a step to destroy excess oxidation reagent in the organic layer by contacting the organic layer with a metal or a nonmetal catalyst.

26. The method of claim 22, wherein the oxidation reagent is hydrogen peroxide.

27. The method of claim 22, wherein the aqueous solution contains 0.1% to 30% oxidation reagent.

28. The method of claim 23, wherein the aqueous solution contains 3% to 5% oxidation reagent.

29. The method of claim 22, wherein the aqueous solution further comprises an acid.

30. The method of claim 29, wherein the aqueous solution contains 0.1% to 15% acid.

31. The method of claim 29, wherein the acid is selected from the group consisting of acetic acid, hydrochloric acid, nitric acid, phosphoric acid and sulfuric acid.

32. The method of claim 22, wherein the acceptable extraction agent is selected from the group consisting of lower acetates, lower ketones, lower ether, lower alcohols and benzenes.

33. The method of claim 22, wherein the acceptable aqueous salt or hydroxide solution is a solution of a salt or hydroxide selected from the group consisting of ammonium chloride, sodium carbonate, sodium bicarbonate, potassium carbonate, sodium hydroxide, potassium hydroxide, sodium thiosulfate, sodium sulfite and sodium hydrosulfide.

34. The method of claim 22, wherein the acceptable aqueous salt or hydroxide solution is a solution of a salt selected from the group consisting of sodium thiosulfate, sodium sulfite and sodium hydrosulfide.

35. The method of claim 22, wherein the acceptable aqueous salt solution is an aqueous alkali salt or hydroxide solution.

36. The method of claim 22, wherein the alkali aqueous salt or hydroxide solution has a pH of between about 7 and 14.

37. The method of claim 35, wherein the aqueous alkali salt or hydroxide solution is an aqueous alkali hydroxide solution selected from the group consisting of a sodium hydroxide solution and a potassium hydroxide solution.

38. The method of claim 22, further comprising a second washing step to wash the organic layer with an acceptable aqueous salt or hydroxide solution.

39. The method of claim 38, wherein the acceptable aqueous salt or hydroxide solutions in the second wash step is a solution of a salt or hydroxide selected from the group consisting of ammonium chloride, sodium carbonate, sodium bicarbonate, potassium carbonate, sodium hydroxide, potassium hydroxide, sodium thiosulfate, sodium sulfite and sodium hydrosulfide.

40. The method of claim 38, wherein the second washing step is performed with a solution that is different from the solution used in the first washing step.

41. The method of claim 22, wherein the dried extract contains more than 50% by weight terpene trilactones.

42. The method of claim 22, further comprising a step of recrystallizing the extract containing terpene trilactones to obtain terpene trilactones in higher purity.

43. A method of isolating terpene trilactones from *Ginkgo biloba* plant material or extract comprising the steps of:
   suspending the plant material or extract in an aqueous solution of hydrogen peroxide;
   adjusting the pH of the suspended plant material or extract in aqueous solution to a pH of between 4 and 6.5;
   extracting the terpene trilactones using an acceptable extraction agent;
   separating the organic layer from the aqueous layer;
   washing the organic layer with an aqueous alkaline salt or hydroxide solution;
   drying the organic layer to form a dried extract containing terpene trilactones; and
   recrystallizing the dried extract containing terpene trilactones to obtain terpene trilactones in higher purity.

44. The method of claim 43, further comprising a step of heating or boiling the suspended plant material or extract in aqueous solution for a period of time between 5 minutes and 5 hours.

45. The method of claim 43, further comprising a step to destroy excess oxidation reagent in the organic layer by contacting the organic layer with a metal or a nonmetal catalyst.

46. The method of claim 43, wherein the aqueous solution contains 0.1% to 30% hydrogen peroxide.

47. The method of claim 43, wherein the aqueous solution contains 0.1% to 15% acid.

48. The method of claim 47, wherein the acid is selected from the group consisting of acetic acid, hydrochloric acid, nitric acid, phosphoric acid and sulfuric acid.

49. The method of claim 43, wherein the acceptable extraction agent is selected from the group consisting of lower acetates, lower ketones, lower ether, lower alcohols and benzenes.

50. The method of claim 43, wherein the aqueous alkaline salt or hydroxide solution is a solution of a salt selected from the group consisting of sodium thiosulfate, sodium sulfite and sodium hydrosulfide.

51. The method of claim 43, wherein the aqueous alkaline salt or hydroxide solution has a pH of between about 8.3 and 9.3.

52. The method of claim 43, further comprising a second washing step to wash the organic layer with an acceptable aqueous salt or hydroxide solution.

53. The method of claim 52, wherein the acceptable aqueous salt or hydroxide solutions in the second wash step is a solution of a salt or hydroxide selected from the group consisting of ammonium chloride, sodium carbonate, sodium bicarbonate, potassium carbonate, sodium hydroxide, potassium hydroxide, sodium thiosulfate, sodium sulfite and sodium hydrosulfide.

54. The method of claim 53, wherein the second washing step is performed with a solution that is different from the solution used in the first washing step.

55. The method of claim 43, wherein the dried extract contains more than 50% by weight terpene trilactones.

56. A method of isolating terpene trilactones from *Ginkgo biloba* plant material or extract comprising the steps of:

suspending the plant material or extract in water;

extracting the terpene trilactones using an acceptable extraction agent;

separating the organic layer from the aqueous layer;

washing the organic layer with an aqueous alkaline salt or hydroxide solution to thereby isolate the terpene trilactones in the organic layer.

57. The method of claim 56, wherein the acceptable extraction agent is selected from the group consisting of lower acetates, lower ketones, lower ether, lower alcohols and benzenes.

58. The method of claim 56, wherein the separation is performed with the addition of sodium chloride to the emulsion containing organic and aqueous layers.

59. The method of claim 56, wherein the aqueous alkaline salt or hydroxide solution in the washing step is a solution of a salt or hydroxide selected from the group consisting of sodium thiosulfate, sodium sulfite and sodium hydrosulfide.

60. The method of claim 56, wherein the aqueous alkaline salt solution is a sodium sulfite solution.

61. The method of claim 56, wherein the aqueous alkaline salt solution in the washing step has a pH of between about 7.5 and 9.5.

62. The method of claim 56, wherein the aqueous alkali salt or hydroxide solution is an aqueous alkali hydroxide solution selected from the group consisting of a sodium hydroxide solution and a potassium hydroxide solution.

63. The method of claim 56, further comprising a second washing step to wash the organic layer with an acceptable aqueous salt or hydroxide solution.

64. The method of claim 63, wherein the acceptable aqueous salt or hydroxide solutions of the second wash step is selected from the group consisting of ammonium chloride, sodium carbonate, sodium bicarbonate, potassium carbonate, sodium hydroxide, potassium hydroxide, sodium thiosulfate, sodium sulfite and sodium hydrosulfide.

65. The method of claim 63, wherein the second washing step is performed with a solution that is different from the solution used in the first washing step.

66. The method of claim 56, further comprising the step of adjusting the pH of the suspended plant material or extract in aqueous solution to a pH of between 4 and 6.5.

67. The method of claim 66, wherein the pH is adjusted by addition of an acid selected from the group consisting of acetic acid, hydrochloric acid, nitric acid, phosphoric acid and sulfuric acid.

68. The method of claim 56, further comprising a step of drying the organic layer to form an extract containing terpene trilactones.

69. The method of claim 68, wherein the extract contains more than 50% by weight terpene trilactones.

70. The method of claim 68, further comprising a step of recrystallizing the extract containing terpene trilactones to obtain terpene trilactones in higher purity.

71. The method of claim 1, 22, 43 or 56, further comprising a step of purifying the isolated terpene trilactones by reversed phase chromatography.

* * * * *